United States Patent [19]

Palitsch et al.

[11] Patent Number: 5,110,923

[45] Date of Patent: May 5, 1992

[54] METHOD FOR PREPARING 5-CHLOROCARBONYL-5H-DIBENZ(B,-F)AZEPINE

[75] Inventors: Peter Palitsch, Dresden; Klaus Czernotzky, Radebeul; Erhard Richter, Radebeul; Berndt Kreher, Radebeul; Wilifried Klump, deceased, late of Bad Suderode, by Dagmar Klump, heir; Rainer Müller, Dresden, all of Fed. Rep. of Germany

[73] Assignee: Arzneimittelwerk Dresden GmbH, Radebeul, Fed. Rep. of Germany

[21] Appl. No.: 687,398

[22] Filed: Apr. 18, 1991

[30] Foreign Application Priority Data

Jul. 18, 1990 [DE] Fed. Rep. of Germany ....... 4023204

[51] Int. Cl.⁵ .......................................... C07D 223/26
[52] U.S. Cl. .................................................... 540/589
[58] Field of Search ........................................ 540/589

[56] References Cited

U.S. PATENT DOCUMENTS 3,905,957  9/1975  Sirrenberg et al. ................. 540/589
4,659,817  4/1987  Gallop ................................. 540/598

*Primary Examiner*—John M. Ford
*Attorney, Agent, or Firm*—Schweitzer Cornman & Gross

[57] ABSTRACT

The invention is directed to a process for the synthesis of 5-chlorocarbonyl-5H-dibenz[b,f]azepine, which is the precursor for the industrial scale synthesis of 5-carbamoyl-5H-dibenz[b,f]azepine. The latter substance is used as pharmaceutical compound. In the process phosgene is passed into a suspension of iminostilbene in an inert solvent at 20° C.–60° C. until the iminostilbene reacted to form an almost equimolar mixture of 5-chlorocarbonyl-5H-dibenz[b,f]azepine and iminostilbene hydrochloride, and then iminostilbene is released from the iminostilbene hydrochloride by the addition of an aqueous base. The iminostilbene so released is also made available for a complete phosgenation while an acidic reaction environment is maintained. After the iminostilbene reacted completely, the reaction mixture is heated slowly to 20° C.–90° C. with stirring and is detoxified by the hydrochloric acid that is formed.

11 Claims, No Drawings

METHOD FOR PREPARING 5-CHLOROCARBONYL-5H-DIBENZ(B,F)AZEPINE

FIELD OF THE INVENTION

The present invention relates to a method for preparing 5-chlorocarbonyl-5H-dibenz[b,f azepine of formula (I) (hereinafter "CCDA").

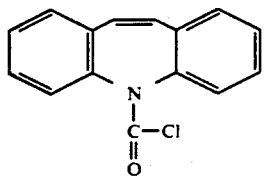

This compound is the precursor for preparing 5-carbamoyl-5H-dibenz[b,f]azepine of formula (II) (hereinafter "carbamazepine")

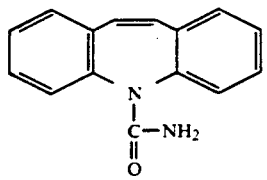

5-carbamoyl-5H-dibenz[b,f]azepine is a pharmaceutically active compound, best known as an analgesic and anticonvulsant.

Both the process of the present invention, and its aforementioned use as a precursor, are suitable for large scale industrial production.

BACKGROUND OF THE INVENTION

The preparation of 5-chlorocarbonyl-5H-dibenz[b,f]azepine (CCDA) (I) from iminostilbene or 5H-dibenz[b,f]azepine of formula (III)

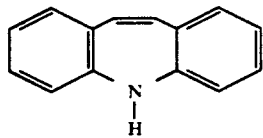

was described for the first time by W. Schindler in German DAS No. 1,136,707, and in Swiss patent No. 54,023.

According to this method, the iminostilbene of formula (III) is suspended in toluene. Phosgene is introduced into the suspension while heating the reaction mixture to 70° C. Then the reaction mixture is refluxed during the further addition of phosgene, and is kept at boiling until the iminostilbene completely reacted and the evolution of hydrogen chloride has ceased. The introduction of phosgene is discontinued as soon as the reaction solution is free of iminostilbene. Excess phosgene is removed from the reaction mixture with dry nitrogen or dry air, such as is described in German DAS No. 1,001,271, in which the excess phosgene is blown out with dry air at the end of the phosgenation of 5H-10,11-dihydro-dibenz[b,f]azepine, or iminodibenzyl.

The so detoxified reaction solution, is worked up in a manner known per se and then the CCDA of formula (I) is recovered by crystallization is amidized in a manner known per se to the carbamazepine of formula (II). The known methods all use an inert, anhydrous solvent such as toluene, chlorobenzene or o-dichlorobenzene at temperatures above 100° C. See, for example, the patents referred to in the survey article by B. Renfroe, C. Harrington and G. R. Proctor in "Heterocyclic Compounds", Vol. 43, "Azepines", part I, published by John Wiley & Sons, NY, 1984, page 524, Table 118.

In all known industrial methods the iminostilbene hydrochloride formed by the phosgenation is thermally dissociated into hydrogen chloride gas and free iminostilbene. This is carried out by heating the reaction mixture to the boiling point in an inert solvent, and introducting phosgene under reflux conditions.

The known high temperature phosgenations are all carried out at 100° C. and higher temperatures, to achieve a complete phosgenation of the iminostilbene, or the iminodibenzyl.

The known methods of synthesizing carbamic acid chlorides from secondary amines are summarized in a table in the Houben-Weyl organic chemistry methodology mannual (vol. E 4, pages 46–50, Georg Thieme Verlag, Stuttgart, N.Y., Publisher, 1983). Usually especially aromatic hydrocarbons, such as benzene, toluene or chlorobenzene are used as solvent. Methods have also been described, in which the reaction is carried out in chloroform, in 1,4-dioxane, and in ethyl acetate. If the reaction is carried out at low temperatures, only half of the amine is converted into the desired carbamic acid chloride when the phosgene is passed into a solution of the secondary amine in an inert solvent. This is because the hydrogen chloride liberated during the reaction, converts the other half of the amine into the hydrochloride. The amine hydrochloride precipitates in crystalline form. Therefore, the yield of the carbamic acid chloride can even in the most favorable case amount only to 50%.

Since the work of H. Erdmann and P. Huth (J. Prakt. Chem. (2) 56, 7, 1897), it is known that the conversion can be completed if an inert, anhydrous base, such as pyridine, is used in an at least equimolar amount.

According to Houben-Weyl (see above) in addition to pyridine, triethylamine and of course, the amine itself that is to be reacted are suitable as inert bases. The cold phosgenation becomes more costly since at least equimolar amounts of inert base are always required. The process is costly because the amine hydrochloride has to be separated out for recovering the inert base. Therefore, the cold phosgenation in the presence of inert auxiliary bases is of importance only for the reaction of temperature sensitive, secondary amines, which increasingly tend to undergo undersirable side reactions at the high temperatures of the hot phosgenation.

In industry, the reaction is preferably carried out at temperatures above 100° C. In this connection Houben-Weyl (see above) states that "[A]dvantageously, the reaction mixture is heated to temperatures above 100° C. while further phosgene is introduced, and the entire amine chloride is converted into the carbamic acid chloride." In this thermal dissociation the hydrogen chloride gas carries along appreciable amounts of phosgene. Therefore, the off-gas decontamination must be detoxified and destroyed in special off-gas equipment. Such a procedure can seriously endanger the environment in the case of an accident, because of the danger presented by the extremely poisonous nature of phosgene which is a gas under ambient conditions.

The procedure of high temperature phosgenation has, the following more significant serious disadvantages:
the burden of having to deal with large amounts of liberated hydrogen chloride off-gas, including phosgene, and the entrained solvent vapors, and the resulting environmental protection problems;
long reaction times of more than 18-24 hours in contact with highly corrosive media;
a number of side reactions, and the dark coloration of the reaction product resulting in a low quality of the carbamazepine end product; and
increasing formation of unwanted 9-methylacridine byproduct temperatures above 90° C. represents a contraction of the 7-membered ring of the iminostilbene.

Only at temperatures of about 90° C. does the thermal dissociation of the iminostilbene hydrochloride into free iminostilbene and hydrogen chloride gas proceed sufficiently rapidly to achieve reaction times, which are acceptable for industrial purposes. However, iminostilbene is a temperature sensitive amine. Therefore, iminostilbene is suitably phosgenated by the method of Schnidler described in the aforementioned German DAS No. 1,136,707.

The process variant preferred by Schindler is dividing the phosgenation into two stages, a cold phosgenation stage resulting in an about 50% conversion in the first phase, and a hot phosgenating stage. Conversion carried out in a second stage has clear advantages over a direct single stage hot phosgenation, because the yields are appreciably increased in this manner, the side reactions that take place above 90° C. are suppressed, and the quality and color of the end product are improved. Nevertheless, the aforementioned disadvantages continue to exist in the second stage of the reaction, i.e. from the start of the heating to 90° C. and during the thermal dissociation of the iminostilbene hydrochloride until the end of the reaction.

An excess of phosgene is introduced into the reaction mixture to utilize the gentle reaction conditions of the first, the cold phosgenating stage as much as possible. A pressure surge can occur if the reaction mixture is heated subsequently to dissociate thermally the iminostilbene hydrochloride. This dangerous possibility is also mentioned in Houben-Weyl (volume E 4, page 744).

When a pressure surge occurs, the spontaneously released hydrogen chloride gas also carries along appreciable amounts of phosgene. Therefore, the apparatus for destroying or detoxifying the off-gases must be sufficiently large to avoid the release of phosgene into the atmosphere.

The reaction is advisably carried out at temperatures of between 90° C. and 100° C. to suppress the unwanted side reactions and the formation of the methylacridine byproduct. The phosgenation proceeds sufficiently rapidly at this temperature. However, the partial pressure of the phosgene is appreciably increased at the higher temperature, compared to that of the cold phosgenation, therefore it is not possible to prevent the steady escape of large quantities of phosgene being carried along by the liberated hydrogen chloride. This can, of course, be also realized from the fact that appreciably less time is required for the conversion of the first half of the iminostilbene in the cold phosgenation stage, than for the conversion of the second half in the hot phosgenation stage.

The reaciton solution has to be detoxified after the complete conversion of the iminostilbene. The excess phosgene is blown out of the reaction solution with dry nitrogen as a rule, or a portion of the solvent is distilled off until the reaction mixture is free of phosgene. This detoxification method has the disadvantage that phosgene can leak into the atmosphere if there are any leaks due to the high gas pressure in the apparatus. Therefore, in the long run there is a constant danger of atmospheric contamination by the escaping phosgene.

Other methods are also known for preparing CCDA. These other methods start from 10,11-dihydro-5H-dibenz[b,f]azepine, or iminodibenzyl of formula (IV)

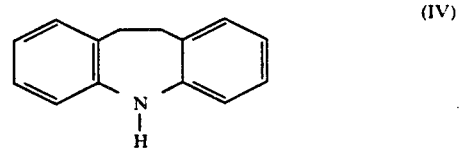

In this connection see British patent No. 1,246,606 and East German patents Nos. 82,719; 100,948; 101,671; 102,149; 102,150; 102,151; 108,535; 133,052; 234,862 Al; and 234,863 Al. According to the methods described in these references, iminodibenzyl is reacted with phosgene in a boiling, inert, aromatic solvent, preferably toluene, or chlorobenzene. Phosgene is introduced into the refluxing material. Thus these methods also employ hot phosgenation with all of its attendant disadvantages.

The resulting 5-chlorocarbonyl-5H-10,11-dibenz[b,f]-azepine of formula (V)

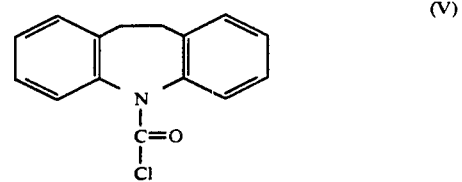

is reacted in an inert organic solvent with elemental bromine, or is otherwise subjected to selective bromination and the corresponding 10-monobromo derivative formula (VI)

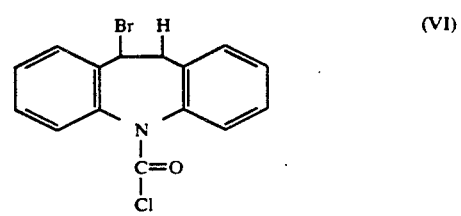

and/or the 10,11-dibromo-derivative formula (VII)

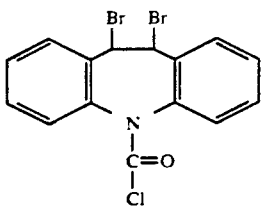

(VII)

is formed.

The bromo compounds (VI) and/or (VII) are subsequently dehydrobrominated and/or are thermally debrominated. A partial exchange (30–40%) of the chlorine atom of the 5-chlorocarbonyl group for a bromine atom takes place during such a thermal process. Due to the required high reaction temperatures (150° C.–170° C.) and because of the liberated bromine, these drastic reaction conditions necessarily lead to uncontrollable side reactions, such as bromination of the ring, resinification, cracking, and discoloration.

Thus the CCDA prepared by these processes contains, in addition to numerous, particularly bromine-containing, byproducts also some greasy, tarry, colored contaminants, the removal of which requires an undue effort.

The nature and structure of these byproducts is not known. The customary purification methods lead to appreciable losses.

No purification method was known until now, which can economically solve the problem of the residual bromine content. Thus, as determinedly high pressure liquid chromatography, the CCDA so prepared is present the average in an amount of 90%, and the precursor for the carbamazepine end product, contains about 10% impurities.

DESCRIPTION OF THE INVENTION

The objective of the invention is to prepare CCDA, or 5-chlorocarbonyl-5H-dibenz[b,f]azepine of formula (I) from iminostilbene, or 5H-dibenz[b,f]azepine of formula (III) under most gentle and mild reaction conditions in quantitative yield and in a significantly better quality than has been possible in the prior art. The process of the present invention accomplishes this in a significantly shorter reaction time and with an appreciably lesser need for energy. The hot phogenation phase or the thermal dissociation of the iminostilbene hydrochloride of the prior art processes, is avoided. Thus, the process of the present invention is environmental more safe. Furthermore, the reaction is conducted so that the emission of phosgene is eliminated and a self-detoxification of the reaction solution takes place.

The foregoing objective is accomplished in accordance with the present invention, by including phosgene or a solution of phosgene in an inert solvent, into a suspension of iminostilbene in the same kind of solvent at from about 20° C. to about 60° C. until the iminostilbene is converted into an almost equimolar mixture of CCDA and iminostilbene hydrochloride. Thereupon the iminostilbene is released from the thus formed iminostilbene hydrochloride, by the addition of an aqueous base, to make it available for complete phosgenation while maintaining an acidic reaction environment.

The reaction is suitably carried out at temperatures ranging from about 35° C. to about 50° C. After about 50% of the iminostilbene is reacted to produce the desired carbamic acid chloride, a dilute solution of an alkali hydroxide, or a dilute solution of ammonia water, or an aqueous solution of an alkali carbonate, or hydrogen carbonate, or of an alkaline hydrolyzing salt such as sodium acetate, is introduced into the reaction mass. The introduction of phosgene is maintained until a complete conversion of the iminostilbene, such as indicated by thin layer chromatography. During the inflow of the aqueous base, the temperature is maintained at from about 35° C. to about 50° C.

In the final phase of the phosgenation, the temperature is maintained at from about 40° C. to about 50° C., so that the carbamic acid chloride will not crystallize out. Temperature deviations of a few degrees up or down are of no consequence.

The introduction of phosgene is stopped as soon as iminostilbene can no longer be detected in the reaction solution. The strongly acidic reaction mixture which has about pH 1 is next heated slowly to from about 80° C. to about 90° C. to hydrolyze the excess phosgene by the hydrochloric acid in the aqueous phase. The reaction mixture is detoxified in this manner in a significantly shorter time and more simply than it would be by the blowing-out method of the hot phosgenation, which is carried out with the exclusion of water.

It is most surprising that in the process of the present invention neither the CCDA already formed nor the phosgene, which is introduced, is decomposed to any noticeable extent by the added aqueous base, or by the aqueous hydrochloric phase which is present towards the end of the phosgenation. This is suprising, because as phosgene is detoxified, for example, with a from about 15 to about 20% sodium hydroxide solution as described for example in "Organikum", 6th edition, page 630, 1967 VEB Deutscher Verlag der Wissenschaften, Autorenkollektiv, the CCDA as an alkali sensitive carbamic acid chloride, is also immediately and spontaneously converted in the presence of aqueous alkaline solutions by way of the sodium salt of the carbamic acid in question, and decarboxylation back into the iminostilbene.

It is for these reasons that the secondary amines cannot normally be reacted with phosgene in the presence of aqueous, alkaline solutions. Completely unexpectedly, however, the phosgenation of the iminostilbene proceeds significantly more quickly under the conditions described, which are clearly milder and more gentle. The reaction time is reduced by one half by the process of the present invention.

The formation of byproducts is also suppressed. Surprisingly, only very little 9-methylacridine is formed under the reaction conditions described. Pursuant to the process of the present invention this unwanted byproduct is removed in a very elegant way suitably after the "self-detoxification" and during the phase separation. The detoxified, hot reaction mixture is allowed to stand at from about 80° C. to about 90° C. for some time to permit the phases to separate. The lower, aqueous, strongly acidic phase is removed and discarded. Aside from the respective salt, this aqueous phase contains only about 0.2% of the originally used iminostilbene in the form of various byproducts. It is estimated that about 50% of these by-products is 9-methylacridine, which is present as hydrochloride. Iminostilbene is present in an extremely small amount in the aqueous, acidic solution. The detoxification of the reaction solution by the from about 7 to about 10% hydrochloric acid formed therefore, also has a positive effect, in that amine-like, basic byproducts are extracted in the form of their hydrochloride from the organic phase, that is, the aqueous, acidic phase has a preliminary cleaning effect with respect to the carbamazepine end product.

Suitable as inert solvents are the aromatic hydrocarbons, benzene, toluene or chlorobenzene, as well as the chlorinated, aliphatic hydrocarbons, suitably chloroform, or carbon tetrachloride.

Suitably dilute alkali solutions or dilute ammonia water is used as the base. The use of such a suitable base assures a phosgenation which does not produce any off-gases until almost all of the iminostilbene is reacted, whereby only shortly before the end of the reaction does a slight decomposition of the introduced phosgene occur. This decomposition manifests itself in the evolution of carbon dioxide. The escaping carbon dioxide carries slight quantities of phosgene into the absorption receiver. However, compared to the known hot phosgenation method, these amount to only a small percentage of the phosgene and HCl-containing off-gases, which are otherwise driven off and would have to be detoxified.

Pursuant to the process of the present invention the equimolar amount of the hydrogen chloride released is chemically bound by the added base, while the rest is dissolved in the aqueous phase.

In principle it is also possible to use as the base aqueous solutions of alkali carbonates, or hydrogen carbonates. In this special case, however, the evolution of carbon dioxide commences immediately with the start of the inflow of these solutions into the reaction mixture, so that phosgene reaches the off-gas at the latest after a 50% conversion. Although even in this special case less phosgene is discharged than in the known hot phosgenation process, nevertheless the use of alkali hydroxide solutions or ammonia water is a more suitable base to be employed to the present process.

The use of the bases, however, is not possible at the start of the reaction, because the phosgene is immediately decomposed under alkaline conditions, that is, in the presence of an excess of aqueous solutions of base. However, almost neutral carbonates of low solubility, such as calcium carbonate, can be used initially in the form of an aqueous suspension as an acid collector already at the start of the phosgenation. In this case, however, the evolution of carbon dioxide and the resulting expulsion of phosgene commence in an appreciably more timely manner, than when an aqueous solution of alkali carbonate is used after an about 50% conversion of the iminostilbene. The aqueous solutions of the alkali carbonates or the aqueous suspensions of the alkali hydrogen carbonates or of the alkaline earth carbonates are therefore not so desirable for large scale industrial phosgenations involving batches of up to 600 kg of iminostilbene.

However, in an embodiment of the present invention, an aqueous suspension of the alkaline earth oxide, suitably of calcium oxide or magnesium oxide, or of an alkaline earth hydroxide is introduced after an approximately 50% conversion of the iminostilbene. For one equivalent of iminostilbene from about 0.55 to about 1.00 equivalents of base, but suitably only from about 0.55 to about 0.75 equivalents of base are used. For example, 0.55–0.75 moles of NaOH, KOH or $NH_3$ or 0.28–0.38 moles of CaO are required for 1 mole of iminostilbene.

In a further embodiment of the process of the invention the inflow of the aqueous solution of the base is commenced already after about a from about 10 to about 20% conversion of the iminostilbene, but the rate of the introduction of the phosgene and the rate of adding the aqueous base are to be controlled so that the pH of the reaction mixture never strays into the alkaline region.

The present invention is further disclosed by the following illustrative examples.

EXAMPLE 1

160 Grams (0.835 moles) iminostilbene are suspended in 800 ml toluene. This suspension is heated to 35° C.–40° C. Phosgene is passed into the stirred suspension. The reaction is slightly exothermic. The temperature of the reaction mixture rises to approximately to 50° C. For industrial scale batches, the temperature of the reaction mixture is maintained at 40° C.–50° C. by cooling.

When about 50% of the iminostilbene is converted to the CCDA after a reaction time of about 1.5 hours, the temperature of the reaction mixture no longer rises and the iminostilbene color has disappeared. The slow addition of dilute sodium hydroxide solution (20 g of NaOH, or 0.50 moles, dissolved in 150 ml water) is commenced at this time, while steadily continuing to introduce more phosgene. The addition of the sodium hydroxide solution is concluded after 30–45 minutes. The iminostilbene hydrochloride goes into solution. More phosgene is passed into the solution.

As the reaction progresses, the reaction solution steadily assumes a brighter color. Towards the end of the reaction, the color of the foam of the reaction solution changes from yellowish brown through yellow to white. This white head of foam on the stirred reaction solution and the incipient evolution of carbon dioxide shortly before the end of the reaction are important indications that the conversion of iminostilbene is completed.

Towards the end of the reaction, the temperature is maintained at almost 50° C., so that the chlorocarbonyl-iminostilbene does not crystallize out. The introduction of phosgene is discontinued when iminostilbene can no longer be detected in the reaction solution. Water (100 ml) is added to keep in solution the NaCl that was formed.

The reaction mixture, which has a pH of 1, is then heated slowly from about 50° C. between about 80° C. and 90° C. Any excess phosgene is rapidly decomposed hydrolytically under these conditions.

The lower acidic aqueous phase is removed and discarded as soon as the reaction mixture is free of phosgene. This aqueous phase has a cleaning effect on the CCDA formed, because it contains from about 0.2 to about 0.3 gram of several amine-like byproducts in the form of their hydrochlorides. It particularly contains 9-methylacridine. The amine-like byproducts can be liberated from the aqueous phase with NaOH. If required, the toluene phase can be extracted with dilute hydrochloric acid and then washed with water. After separating the phases once more, the toluene solution of the CCDA is distilled. After removal of the solvent, the remaining liquefied chlorocarbonyl-iminostilbene is precipitated in methanol. The methanolic suspension is cooled down and the crystalline chlorocarbonyl-iminostilbene is filtered off with suction and dried.

Yield is 197–200 g of CCDA (i.e. 93–94% of the theoretical yield);

Melting point is 157° C.–158° C.;

Purity according to high pressure liquid chromatography (HPLC) is 99.8%–100%;

Purity according to thin layer chromatography (TLC) is 99.7%–99.9%.

The CCDA obtained in this manner, is converted into a crude carbamazepine by the known amidation method. Pure carbamazepine is obtained, after a single recrystallization from methanol-water. This meets all the requirements of the various international pharmacopoeias (i.e. maximum concentration of a single impurity $\leq 0.01\%$).

A further 5–10 g of CCDA are obtained by concentrating the mother liquor. The total yield thus is 205–207 g, which corresponds to 96.5–97.5% of the theoretical yield.

The chlorocarbonyl-iminostilbene (CCDA), which is obtained from the methanolic mother liquor, can be collected and worked up separately.

EXAMPLE 2

160 Grams iminostilbene are dissolved in 800 ml toluene. Phosgene is passed into this suspension at about 35° C. to about 40° C. as described in Example 1. After 50% conversion of the iminostilbene, the slow addition of 70 ml of 12.7% ammonia water (density of 0.95 g/cc at 15° C.; and containing 0.50 moles of NH$_3$) is commenced, the introduction of phosgene is steadily continued. The dilute ammonia water is added dropwise over a period of about 1 hour. The introduction of phosgene is continued until the iminostilbene has been completely reacted. Then the reaction solution is slowly heated from about 50° C. to from about 80° C. and about 90° C. and stirring is continued at this temperature until phosgene can no longer be detected. The detoxification requires about 1 hour. The detoxified reaction mixture is then mixed with 100 ml of water to dissolve the ammonium chloride. After that, 4 g of activated charcoal are added. The mixture is stirred for a further hour at 80° C.–90° C. and is subsequently filtered. The charcoal is washed with 50 ml of hot toluene. The aqueous, acidic phase is removed from the filtrate and discarded. The toluene solution is worked up as described in Example 1.

Yield is 195–205 g CCDA (i.e. 92.0–96.5% of the theoretical yield);

Melting point is 157° C.–158° C.;

Purity according to HPLC is 99.8%–100%.

A further 3–10 g of CCDA are obtained from the methanolic mother liquor by concentration.

EXAMPLE 3

160 Grams iminostilbene are suspended in 800 ml of chlorobenzene. This suspension is treated with phosgene as described in Example 1. After 50% of the iminostilbene is converted, the addition of dilute potassium hydroxide solution (30 g KOH or 0.55 moles, dissolved in 170 ml water) is commenced. This alkaline solution is added dropwise and uniformly over a period of about 45 minutes, while phosgene is continuously being introduced.

During phosgenation, the temperature is maintained at 35° C.–45° C., suitably at about 34° C. Since CCDA is more soluble in chlorobenzene than in toluene, it is possible to carry out the reaction at 40° C. without having the reaction product crystallizing out. In toluene, the crystallization of chlorocarbonyl-iminostilbene (II) can be expected to occur at temperatures below 40° C. After the iminostilbene has completely reacted, the reaction mixture is detoxified as in Example with 1, or Example 2, 80 ml of water being added to keep in solution the potassium chloride which was formed. The reaction mixture is then mixed with 4 g activated charcoal, stirred for 1 hour at 80° C.–90° C. and is then filtered.

The charcoal is washed with 50 ml of hot chlorobenzene. The aqueous phase is removed at 80° C.–90° C., if necessary, with the addition of a surface active material to break the emulsion layer, and is then discarded. The chlorobenzene phase is worked up as in Example 1.

Yield is 190–193 g of CCDA (i.e. 90–91.5% of the theoretical yield).

Melting point is 157° C.–158° C.;

Purity according to HPLC is 99.75%–100%.

A further 10–15 g of CCDA are obtained from the methanolic mother liquor.

EXAMPLE 4

160 Grams iminostilbene are suspended in 800 ml chlorobenzene and treated with phosgene at about 35° C. to about 50° C. until the iminostilbene color disappeared. A solution of 41 g (0.50 moles) of sodium acetate in 150 ml of water is added dropwise over a period of one hour to the approximately equimolar mixture of CCDA and iminostilbene hydrochloride, while phosgene continues to be passed into the reaction mixture. The temperature of the reaction mixture may fall to 40° C. during this time. At about 40° C. to about 45° C. after the addition of the acetate solution, more phosgene is passed in until the iminostilbene has been completely converted. The reaction solution then is heated to from about 80° C. to about 90° C. and is detoxified. The phosgene-free reaction mixture is transferred to a separating funnel. After removal of the aqueous phase, in which the odor of acetic acid can be detected, the chlorobenzene solution is worked up as described in either one of Examples 1 to 3.

Yield is 192–194 g of CCDA (i.e. 90.5–91.5% of the theoretical yield);

Melting point is 156° C.–158° C.

EXAMPLE 5

160 Grams iminostilbene are suspended in 800 ml of toluene and reacted with phosgene as in Example 1. After 50% of the iminostilbene has been converted, the slow addition of 14 g (0.25 moles) of CaO in 170 ml water is commenced while stirring the suspension to keep it homogeneous. Phosgene continues to be introduced during this time. The addition of the CaO-water suspension takes place in about 45 minutes.

Phosgene continues to be introduced into the reaction mixture until all of the iminostilbene is reacted, while the temperature is maintained at 40° C. to 45° C., to the extend possible. The reaction mixture is detoxified in the usual manner and then worked up as described in Example 1.

Yield is 197–201 g of CCDA (i.e. 93–94.5% of the theoretical yield).

A further 5–10 g of CCDA are obtained by working up the methanolic mother liquor.

EXAMPLE 6

160 Grams iminostilbene are suspended in 800 ml toluene. The introduction of phosgene is commenced at 40° C. After 10–20% of the iminostilbene is converted, dilute sodium hydroxide solution (24 g NaOH or 0.60 moles, dissolved in 200 ml water) is slowly added. The rate of addition of the phosgene and the amount of dilute sodium hydroxide solution added are such that the pH of the reaction mixture during the addition of the sodium hydroxide solution should not stray into the alkaline region. The phosgenation is carried out at 40° C.-50° C. After the iminostilbene is completely converted, the reaction mixture is worked up as in Example 1.

Yield is 197-200 g of CCDA (i.e. 93-94% of the theoretical yield):

Melting point is 157° C.-158° C.

We claim:

1. A process for preparing 5-chlorocarbonyl-5H-dibenz[b,f]-azepine of formula (I)

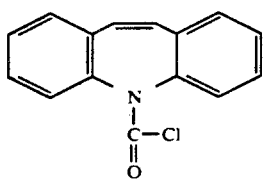

(I)

which comprises reacting in a solvent iminostilbene of formula (III)

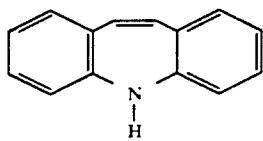

(III)

with phosgene in an anhydrous aromatic solvent, the reaction being carried out at a temperature of from about 20° C. to about 60° C., adding an aqueous base to the reaction to release from the iminostilbene hydrochloride iminostilbene which is formed in addition to the 5-chlorocarbonyl-5H-dibenz[b,f]azepine, and phosgenating the iminostilbene completely while retaining acidic reaction conditions.

2. The process of claim 1, wherein sufficient phosgene is passed into the iminostilbene so that an equimolar or almost equimolar mixture of 5-chlorocarbonyl-5H-dibenz[b,f]azepine and iminostilbene hydrochloride is formed.

3. The process of claim 1, wherein said temperature is from about 35° C. to about 50° C.

4. The process of claims 1 wherein said aqueous base is an aqueous solution of at least one of an alkali hydroxide, ammonia, alkaline hydrolyzing salt, and an aqueous suspension of an alkaline earth hydroxide or oxide.

5. The process of claim 1, wherein the inert solvent is one or more of an aromatic compound, and a halogenated aromatic compound.

6. The process of claim 5, wherein said halogenated aromatic compound is chlorobenzene.

7. The process of claim 1 wherein from about 0.5 to about 1.0 equivalents of base are used per equivalent of iminostilbene.

8. The process of claim 7, wherein from about 0.55 to about 0.75 equivalents are used.

9. A process for preparing the end product 5-chlorocarbonyl-5H-dibenz[b,f]azepine, which comprises phosgenating iminostilbene by introducing phosgene, or a solution of phosgene in an inert solvent into the iminostilbene at a temperature of from about 20° C. to about 60° C. until said iminostilbene is substantially converted into equimolar or nearly equimolar amounts of said end product and iminonistilbene hydrochloride, then adding an aqueous base to release iminostilbene from said iminostilbene hydrochloride, and continuing phosgenation to convert said released iminostilbene while maintaining a substantially acid pH, until a substantially complete conversion of iminostilbene.

10. The process of claim 10, wherein said temperature is from about 35° C. to about 50° C.

11. The process of claim 9, further comprising heating the reaction mixture to from about 80° C. to about 90° C. to hydrolyze the excess phosgene and thus to detoxify the solution.

* * * * *